(12) United States Patent
Bedrio

(10) Patent No.: US 10,610,862 B2
(45) Date of Patent: Apr. 7, 2020

(54) MULTIPLE PATH SAMPLE COLLECTION CARD

(71) Applicant: Advance Dx, Inc., Skokie, IL (US)

(72) Inventor: Ned Bedrio, Scottsdale, AZ (US)

(73) Assignee: Advance Dx, Inc., Scottsdale, AZ (US)

( * ) Notice: Subject to any disclaimer, the term of this patent is extended or adjusted under 35 U.S.C. 154(b) by 534 days.

(21) Appl. No.: 15/089,847

(22) Filed: Apr. 4, 2016

(65) Prior Publication Data

US 2017/0282177 A1 Oct. 5, 2017

(51) Int. Cl.
*B01L 3/00* (2006.01)
*A61B 5/15* (2006.01)
*G01N 1/00* (2006.01)

(52) U.S. Cl.
CPC ...... *B01L 3/5023* (2013.01); *A61B 5/150022* (2013.01); *A61B 5/150358* (2013.01); *B01L 2200/185* (2013.01); *B01L 2300/02* (2013.01); *B01L 2300/069* (2013.01); *B01L 2300/0816* (2013.01); *B01L 2300/0825* (2013.01); *B01L 2300/0864* (2013.01); *B01L 2300/0887* (2013.01); *G01N 2001/005* (2013.01)

(58) Field of Classification Search
CPC .......... B01L 3/5023; B01L 2300/0887; B01L 2300/0816; B01L 2300/069; B01L 2200/185; B01L 2300/0864; B01L 2300/02; B01L 2300/0825; G01N 1/2813; G01N 1/18; G01N 2001/2826; G01N 2001/005; A61B 5/150358; A61B 5/150022
See application file for complete search history.

(56) References Cited

U.S. PATENT DOCUMENTS

| | | | |
|---|---|---|---|
| 4,055,394 A | 10/1977 | Friedman et al. |
| 4,678,757 A | 7/1987 | Rapkin et al. |
| 4,933,092 A | 6/1990 | Aunet et al. |
| 4,943,522 A | 7/1990 | Eisinger et al. |
| 4,999,285 A | 3/1991 | Stiso |
| 5,064,541 A | 11/1991 | Jeng et al. |
| 5,208,163 A | 5/1993 | Charlton et al. |

(Continued)

FOREIGN PATENT DOCUMENTS

| | | |
|---|---|---|
| DE | 4341005 | 6/1995 |
| EP | 0183442 | 6/1986 |

(Continued)

OTHER PUBLICATIONS

International Search Report of PCT/US08/63707 dated Aug. 7, 2008 (2 pages).

(Continued)

*Primary Examiner* — Dennis White
(74) *Attorney, Agent, or Firm* — Maginot, Moore & Beck, LLP

(57) ABSTRACT

A fluid sample collection card in one embodiment includes an absorbent strip including a sample application portion, a first absorbent strip portion extending directly from the sample application portion, and a second absorbent strip portion extending directly from the sample application portion and spaced apart from the first absorbent strip portion by the sample application portion, a non-absorbent layer positioned beneath the absorbent strip, and a sample application portion indicium configured to identify the sample application portion.

8 Claims, 4 Drawing Sheets

(56) References Cited

U.S. PATENT DOCUMENTS

| | | |
|---|---|---|
| 5,409,664 A | 4/1995 | Allen |
| 5,435,970 A | 7/1995 | Mamenta et al. |
| 5,468,648 A * | 11/1995 | Chandler .............. B01L 3/5023 |
| | | 422/408 |
| 5,547,873 A | 8/1996 | Magneson et al. |
| 5,589,399 A | 12/1996 | Allen et al. |
| 5,866,007 A | 2/1999 | Whitson et al. |
| 5,916,521 A | 6/1999 | Bunce et al. |
| 6,258,045 B1 | 7/2001 | Ray et al. |
| 6,316,205 B1 | 11/2001 | Guan et al. |
| 6,357,583 B1 | 3/2002 | Rainen |
| 6,365,417 B1 | 4/2002 | Fleming et al. |
| 6,465,202 B1 | 10/2002 | Tyrrell |
| 6,524,533 B1 | 2/2003 | Tyrrell |
| 7,115,421 B2 | 10/2006 | Grzeda et al. |
| RE39,664 E | 5/2007 | Gordon et al. |
| 7,268,179 B2 | 9/2007 | Brown |
| D560,811 S | 1/2008 | Powell et al. |
| 7,838,258 B2 | 11/2010 | Yang et al. |
| 7,867,780 B2 | 1/2011 | Jones et al. |
| 8,062,608 B2 | 11/2011 | Pankow |
| 8,309,366 B2 | 11/2012 | Buchanan |
| 2002/0192835 A1 | 12/2002 | Cho et al. |
| 2004/0023399 A1 | 2/2004 | Grzeda et al. |
| 2005/0130236 A1 | 6/2005 | Goldman |
| 2006/0008847 A1* | 1/2006 | Ramel .................. B01L 3/5023 |
| | | 435/7.1 |
| 2006/0115805 A1 | 6/2006 | Hansen et al. |
| 2007/0048345 A1 | 3/2007 | Huang et al. |
| 2008/0210644 A1 | 9/2008 | Milunic et al. |
| 2008/0286150 A1* | 11/2008 | Pankow ................ B01L 3/5023 |
| | | 422/400 |
| 2009/0117660 A1 | 5/2009 | Dai et al. |
| 2012/0282634 A1 | 11/2012 | Hughes et al. |

FOREIGN PATENT DOCUMENTS

| | | | |
|---|---|---|---|
| EP | 0806666 | 11/1997 | |
| EP | 1387170 | 2/2004 | |
| WO | 9641817 A1 | 12/1996 | |
| WO | 0136974 | 5/2001 | |
| WO | WO2004097418 A1 | 11/2004 | |
| WO | WO-2005116651 A2 * | 12/2005 | ....... G01N 33/54386 |
| WO | WO2005116651 A2 | 12/2005 | |
| WO | 2006083053 | 8/2006 | |

OTHER PUBLICATIONS

European Search Report in corresponding European patent application (i.e. EP 08 75 5539), dated Jul. 7, 2010 (6 pages).
European International Search Report corresponding to European Appl. No. PCT/US2014/034928, dated Aug. 25, 2014 (11 pages).
International Search Report of PCT/US17/025774 dated Jul. 17, 2017 (13 pages).

* cited by examiner

MULTIPLE PATH SAMPLE COLLECTION CARD

FIELD

The present disclosure relates to collection and separation of biological fluids. More particularly the disclosure relates to fluid sample collection devices used for collection and separation of fluids such as blood.

BACKGROUND

Biological samples are frequently used in laboratory and clinical settings to analyze various components in the samples. The biological samples include blood samples, sputum samples, and urine samples. Such samples, for example, are used to determine the levels or concentrations of various components such as HDL, LDL, Cholesterol, hemoglobin, detection of genes using DNA or RNA along with detection of HIV antibodies, or concentrations of drugs.

The biological sample is frequently processed in a liquid form. Accordingly, the liquid sample is collected, handled by the collection facility, transported to a laboratory, and stored pending processing. Activities surrounding a liquid blood sample present various problems including the risk of container breakage or leakage which causes loss of sample and the danger of infection, sample instability during shipment and storage, transport carrier restrictions related to transport of liquid biohazard materials, and collection of significantly more sample than is necessary for testing so as to ensure sufficient sample quantity is available for common methods of serum or plasma preparation and subsequent analysis. Thus, collection of several vials of fluid such as blood from a patient is not uncommon.

Another shortcoming of liquid form samples is that even when a blood or other fluid sample is removed from the body, the concentration of various components within the sample can change over time due to various ongoing reactions. For example, biochemical and cellular changes, such as red blood cells metabolizing plasma glucose for continued cellular respiration, continue in liquid samples.

In response to the shortcomings of liquid sample collection, transport, and processing, various dried sample devices and methods have emerged. In dried sample devices, a biological sample is collected in the form of a drop or two of fluid such as whole blood. The blood is collected on filter paper and allowed to dry prior to leaving the collection facility. One benefit of using dried blood samples is that dried blood samples are not classified as a special shipping required biohazard material and may be transported through the mail system or other common delivery service just as any other package.

Dried fluid samples have the advantage of reducing various reactions, thereby preserving certain components for later analysis. However, when using dried whole blood collection methods, such as collection on Whatman 903 filter paper, as the blood dries, the red cells hemolyze which then becomes mixed with red blood cell membrane cholesterol. The red blood cell membrane cholesterol, which is not normally in the serum portion of the blood, then becomes mixed in with serum cholesterol. Such a mixing may yield a clinically significant increase in a patient cholesterol result.

The transportation and handling of dried fluid samples is thus a significant improvement over transportation and handling of liquid samples. Merely drying a fluid sample does not always ensure the usefulness of the sample. By way of example, in order to perform analysis of certain dissolved blood components a whole blood sample cannot be used. For example, hemoglobin can interfere with serum analytes at the light absorbance in the instrumental step of clinical analyte testing. Accordingly, the red blood cells must first be separated from the blood plasma or serum prior to drying. The most conventional manner of separating serum or plasma from blood cells is by centrifugation. Centrifugation, of course, requires more than a few drops of blood. Additionally, expensive and space consuming equipment must be maintained at the collection site to perform centrifugation.

Various approaches have been developed to provide for separation of blood samples prior to drying of the samples. For example, U.S. Pat. No. 5,064,541, issued to Jeng et al. on Nov. 12, 1991, describes a device which separates plasma from red blood cells that uses an agglutination agent in a filter to clump red blood cells together. The incorporation of an additional biochemical filter in the device adds to the complexity and cost of the device. Additionally, the amount of blood collected may overwhelm the ability of the red blood cell agglutinating agent to work on all of the red blood cells applied in the whole blood sample.

U.S. Pat. No. 4,816,224, issued to Vogel, et al. on Mar. 28, 1989, describes a series of wicking papers and a relative large sample holder with different embodiments that contain many different components. The device is complex and requires significant foot print space when shipping or undergoing sample extraction at a remote laboratory.

U.S. Pat. No. 6,258,045, issued to Ray et al. on Jul. 10, 2001, describes a device which requires tubing for capillary collection of whole blood along with filtration and multiple layers of reactive or non-reactive materials for plasma separation and testing. Capillary collection tubes require a certain level of operator experience and inflict additional pain on the patient when compared to a simple lancet stick. Additionally, the glass tube can be broken or become detached.

Traditional devices for obtaining dried fluid samples further incorporate indirect methods for ensuring that the proper amount of fluid has been collected to allow the desired separation. Some devices incorporate an indicator which changes color or a portion of the strip which provides a chemical reaction. Such devices do not provide an indication of whether or not too large a sample of fluid has been collected.

Therefore, a collecting device that is self-contained and can be used to provide stable dried biological components to a laboratory would be beneficial. Further benefits would be realized if the device is simple to manufacture and provides accurate results. Further benefits would be provided by a device which enables both the sample collector and laboratory personal to visually directly observe the amount of fluids, such as serum or plasma or red blood cells, which have been collected. A device that can be used to separate fluids such as blood into separate components and which is easy to mail without additional charges would also be beneficial. A device which reduces the time needed for separation and drying of a sample would be further beneficial.

SUMMARY

In one embodiment, a fluid sample collection card includes an absorbent strip including a sample application portion, a first absorbent strip portion extending directly from the sample application portion, and a second absorbent strip portion extending directly from the sample application portion and spaced apart from the first absorbent strip portion by the sample application portion, a non-absorbent layer positioned beneath the absorbent strip, and a sample application portion indicium configured to identify the sample application portion.

In one or more embodiments, a fluid sample collection card includes an upper layer including a sample receiving portion, a first sample viewing portion, and a second sample viewing portion.

In one or more embodiments, the sample application portion indicium includes the sample receiving portion, the sample application portion is directly accessible from above the collection card through the sample receiving portion, the first absorbent strip portion is at least partially viewable through the first sample viewing window, and the second absorbent strip portion is at least partially viewable through the second sample viewing window.

In one or more embodiments, the absorbent strip is configured to separate components of a collected sample.

In one or more embodiments, the first sample viewing window is a first opening in the upper layer extending completely through the upper layer, and the second sample viewing window is a second opening in the upper layer extending completely through the upper layer.

In one or more embodiments, the upper layer includes a first indicium associated with a first volume of the collected sample which, when absorbed by the absorbent strip, separates into a first component of the first volume of collected sample along the first absorbent strip portion to an extent sufficient to perform a first test on the first component, and separates into a second component of the first volume of collected sample along the second absorbent strip portion to an extent sufficient to perform a second test on the second component.

In one or more embodiments, the upper layer includes a second indicium associated with a second volume of the collected sample which, when absorbed by the absorbent strip, separates into a first component of the second volume of collected sample along the first absorbent strip portion to an extent sufficient to perform a first test and a second test on the first component, and separates into a second component of the second volume of collected sample along the second absorbent strip portion to an extent sufficient to perform a third test and a fourth test on the second component.

In one embodiment, a method of collecting a fluid sample includes identifying a sample application portion of an absorbent strip of a collection card using a sample application portion indicium, applying a volume of fluid onto the sample application portion of the absorbent strip, moving a first portion of the applied volume of fluid along a first absorbent strip portion extending directly from the sample application portion and positioned on a nonabsorbent layer of the collection card, and moving a second portion of the applied volume of fluid along a second absorbent strip portion extending directly from the sample application portion and positioned on the nonabsorbent layer, wherein the second absorbent strip portion is separated from the first absorbent strip portion by the sample application portion.

In one or more embodiments, identifying the sample application portion includes identifying a sample receiving portion in an upper layer of the collection card, and applying the volume of fluid includes applying the volume of fluid to the sample application portion from above the collection card through the sample receiving portion.

In one or more embodiments, moving the first portion of the applied volume of fluid along the first absorbent strip portion comprises separating a first component of the first portion of the applied volume of fluid along the first absorbent strip portion, and moving the second portion of the applied volume of fluid along the second absorbent strip portion comprises separating a second component of the second portion of the applied volume of fluid along the second absorbent strip portion.

In one or more embodiments, a method of collecting a fluid sample includes drying the separated first component, and drying the separated second component.

In one or more embodiments, drying the separated first component comprises exposing the separated first component directly to atmosphere through a first sample viewing window extending completely though the upper layer, and drying the separated second component comprises exposing the separated second component directly to atmosphere through a second sample viewing window extending completely though the upper layer, the second sample viewing window spaced apart from the first sample viewing window.

In one or more embodiments, a method of collecting a fluid sample includes determining, prior to drying the separated first component, that a sufficient volume of fluid has been applied to the sample application portion to perform a test on the dried first component by viewing a portion of the first portion of the applied volume of fluid in the first absorbent strip portion through a first sample viewing window of the upper layer.

In one or more embodiments, determining that a sufficient volume of fluid has been applied to the sample application portion includes using an indicium of the upper layer to determine that a sufficient volume of fluid has been applied to the sample application portion.

In one embodiment, a method of obtaining a plurality of separated components of a fluid sample includes receiving a collection card with an absorbent strip positioned on a nonabsorbent layer, identifying a first absorbent strip portion on a first side of an identified sample receiving portion of the absorbent strip and spaced apart from the identified sample receiving portion, the first absorbent strip portion including a first separated component of a fluid sample, detaching the identified first absorbent strip portion from the absorbent strip, identifying a second absorbent strip portion on a second side of the identified sample receiving portion of the absorbent strip and spaced apart from the identified sample receiving portion, the second absorbent strip portion separated from the first absorbent strip portion by the sample application portion, the second absorbent strip portion including a second separated component of the fluid sample, and detaching the identified second absorbent strip portion from the absorbent strip.

In one or more embodiments, the first and second separated components of the fluid sample are dried components.

In one or more embodiments, detaching the identified first absorbent strip portion comprises accessing the absorbent strip through a first window extending completely through an upper layer of the collection card, the identified first absorbent strip portion aligned with the first window, and detaching the identified second absorbent strip portion comprises accessing the absorbent strip through a second window extending completely through an upper layer of the collection card, the identified second absorbent strip portion aligned with the second window.

In one or more embodiments, a method of obtaining a plurality of dried separated components of a fluid sample includes separating a first portion of the nonabsorbent layer from the detached first absorbent strip portion, and separating a second portion of the nonabsorbent layer from the detached second absorbent strip portion.

BRIEF DESCRIPTION OF THE DRAWINGS

The present disclosure may take form in various system and method components and arrangement of system and method components. The drawings are only for purposes of illustrating exemplary embodiments and are not to be construed as limiting the disclosure.

DESCRIPTION

Figure 1:
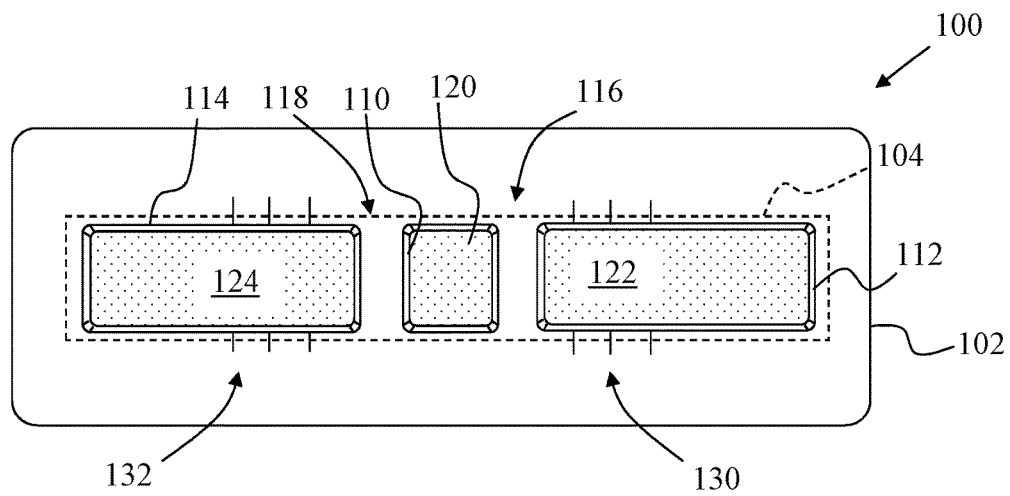
FIG. 1 depicts a top plan view of a collection card including a sample application portion of an absorbent strip accessible through an upper layer of the card and a pair of absorbent strip portions of the absorbent strip viewable through the upper layer of the card in accordance with principles of the disclosure.
Figure 2:
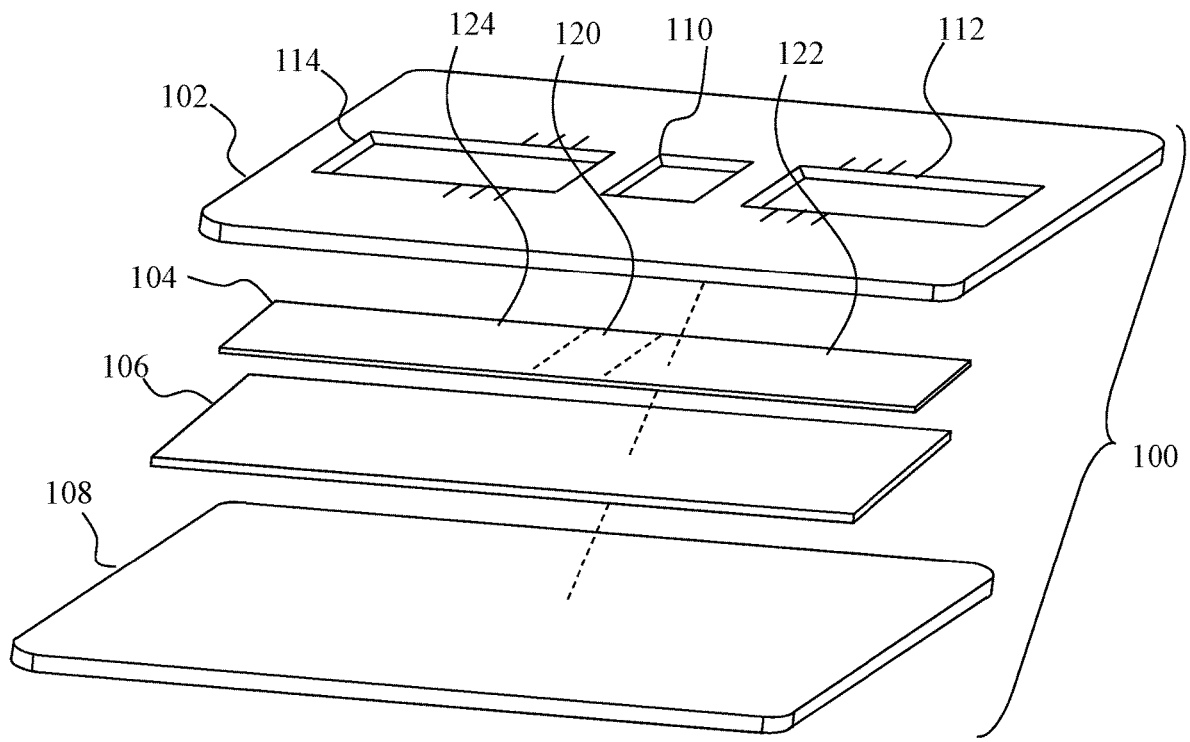
FIG. 2 depicts an exploded perspective view of the card of FIG. 1.

Referring to FIGS. 1 and 2, a fluid sample collection card 100 is shown which in one embodiment is configured to separate serum and plasma components of a fluid blood sample. The fluid sample collection card 100 includes an upper layer 102, an absorbent strip 104, a nonabsorbent layer 106 and a support layer 108. The upper layer 102 includes a sample receiving window 110 and two spaced apart sample viewing windows 112/114. Each of the sample viewing windows 112/114 is spaced apart from the sample receiving window 110 by a respective bridge 116/118.

The sample receiving window 110 is a sample receiving portion of the upper layer 102 which identifies a sample application portion 120 of the absorbent strip 104. In embodiments which do not incorporate an upper layer a sample application portion indicium may be provided by a marking on the nonabsorbent layer 106 or the support layer 108. In some embodiments which include an upper layer but do not include a sample receiving window as a sample application portion indicium (i.e., no bridges), a sample application portion indicium is provided in the form of a marking on the upper layer.

One absorbent strip portion 122 extends directly from one side of the sample application portion 120 while another absorbent strip portion 124 extends directly from the sample application portion 120 from the opposite side of the sample application portion 120. The absorbent strip portion 122 extends beneath the sample viewing window 112 while the absorbent strip portion 124 extends beneath the sample viewing window 114. In the embodiment of FIG. 1, the portions of the absorbent strip portions 122/124 directly beneath the sample viewing windows 112/114 are exposed to atmosphere. In other embodiments, the sample viewing windows include a transparent covering to allow viewing of the portions of the absorbent strip portions 122/124 directly beneath the sample viewing windows 112/114. The transparent material in some embodiments defines the sample receiving window.

The upper layer 102 in one embodiment is fabricated from card stock. Accordingly, a user or manufacturer can easily print data on the upper layer 102. By way of example, a series of reference marks 130 and 132, which extend outwardly from both sides of the sample viewing windows 112/114, are shown on the upper layer 102. Instructions for using the collection card 100 may also be printed on the upper layer, and space for insertion of patient identification data may also be provided therein.

The absorbent strip 104 is sized to be slightly longer than the length of the upper layer 102 between the outer ends of the sample viewing windows 112/114 and slightly wider than the widest of the sample receiving window 110 and the sample viewing windows 112/114. The absorbent strip 104 in this embodiment is configured to separate components of a fluid sample. Accordingly, in one embodiment the absorbent strip 104 is made from LF1 material, commercially available from GE Healthcare Bio-Sciences, Marlborough, Mass. Other suitable material may be used, such as, but not limited to, porous materials that allow liquid and suspended solids to differentially flow and separate based on the molecular size of the molecules.

Additionally, the characteristics of the absorbent strip 104 may be modified by incorporating designs that utilize other physical forces that affect the flow of substances through the absorbent strip 104. Such physical forces include hydrophobic or hydrophilic interactions as well as ionic interactions. Additionally, temporary hydrogen bonding interactions and gravitational effects may be used to augment or retard flow to provide the desired separation or alteration of a separation of the flowing liquids and suspended cells or other solid materials.

The non-absorbent layer 106 is sized to be at least slightly longer and wider than the absorbent strip 104. The non-absorbent layer 106 in one embodiment is Mylar, which is used for its imperviousness to liquid penetration. Other materials which may be used to form an acceptable liquid barrier include thin sheets of Polyethylene, porous UHM-WPE film, FEP film, polyester treated sheeting, ePTF film, and polypropylene.

Assembly of the collection card 100 includes cutting of card stock into the shape of the upper layer 102 and the support layer 108 and forming the sample receiving window 110 and the sample viewing windows 112/114 by press stamping the upper layer 102. The upper layer 102 and the support layer 108 in this embodiment are about 10 centimeters long and about 4.5 centimeters wide.

Figure 3:
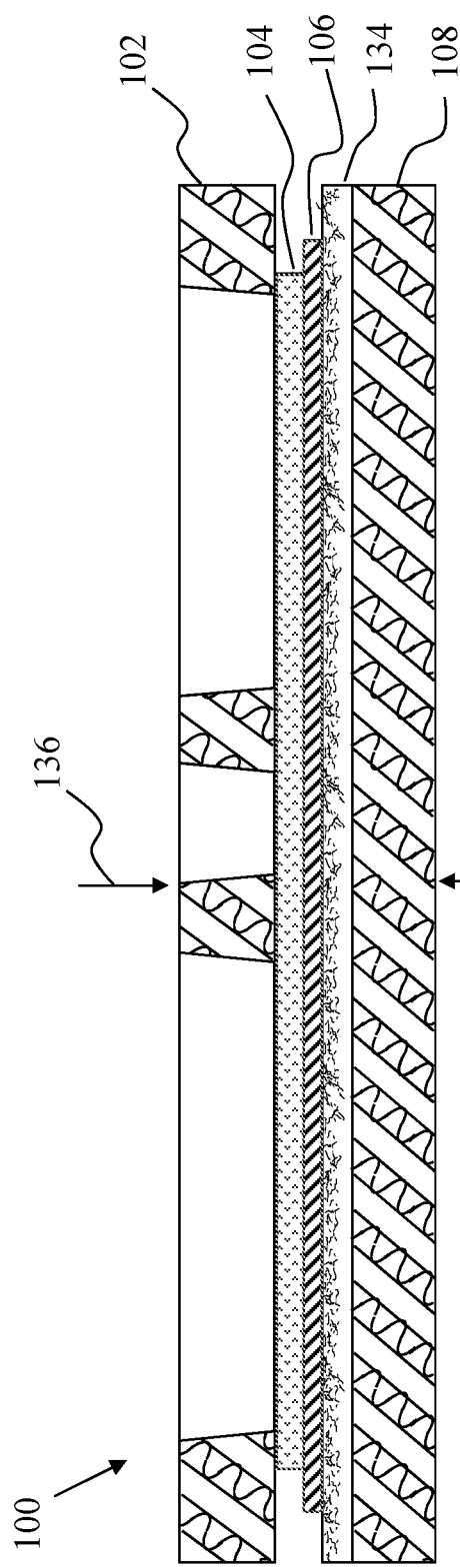
FIG. 3 depicts a side cross-sectional view of the layers of the collection card of FIG. 1 before the upper layer is attached to the support layer by an adhesive layer.

The layers of the collection card 100 in some embodiments are joined by initially applying a layer of adhesive 134 (see FIG. 3) on the support layer 108. Subsequently, the non-absorbent layer 106, the absorbent strip 104 and the upper layer 102 are placed onto the support layer 108 resulting in the configuration of FIG. 3. The collection card 100 is then pressed together as indicated by the arrows 136 and 138 resulting in the configuration of FIG. 4. If desired, heat may also be applied to assist in attaching the upper layer 102 and the non-absorbent layer 106 to the support layer 108.

Figure 4:
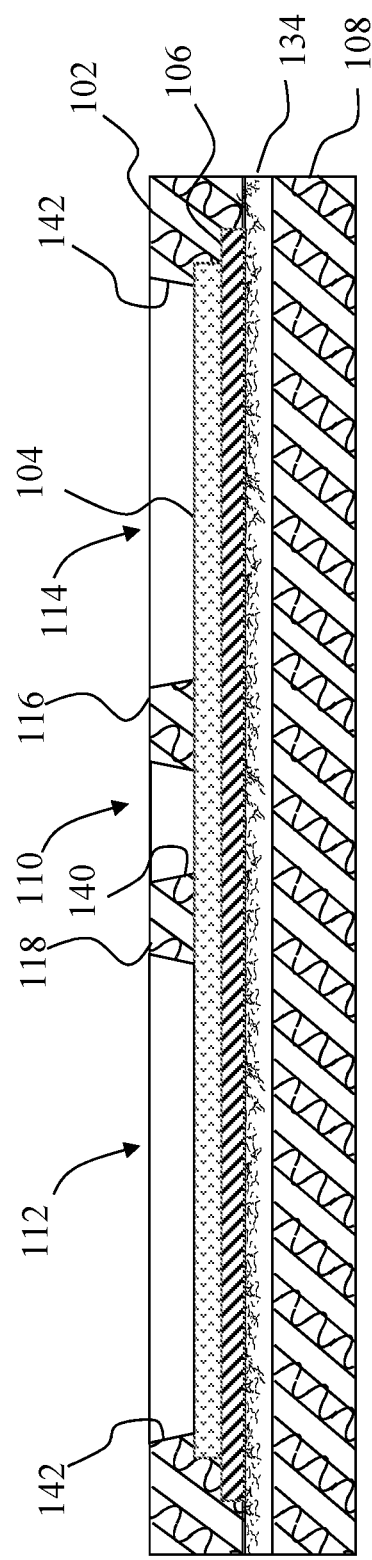
FIG. 4 depicts a side cross-sectional view of the layers of the collection card of FIG. 1 after the upper layer is attached to the support layer by an adhesive layer.

As shown most clearly in FIG. 4, the non-absorbent layer 106 is at least slightly wider and slightly longer than the absorbent strip 104. Accordingly, while the non-absorbent layer 106 is adhered to the support layer 108, the adhesive 124 does not contact the absorbent strip 104. Rather, the absorbent strip 104 is maintained in position by the upper layer 102.

Specifically, the upper layer 102 contacts the adhesive layer 124 completely around the periphery of the non-absorbent layer 106. The absorbent strip 104 is further entrapped by a lip 140 about the sample receiving window 110 and lips 142 about the sample viewing windows 112/114. The bridges 116/118 also entrap the absorbent strip 104 within the collection card 100.

Additionally, pressing of the upper layer 102 against the sandwiched layers (the absorbent strip 104 and the non-absorbent layer 106) causes deformation of the upper layer 102. The deformation includes some amount of compression of the upper layer 102 in an area of the upper layer 102 beginning with the portions of the upper layer 102 which are in contact with the absorbent strip 104 and the non-absorbent layer 106 and extending upwardly from those portions. Accordingly, the portions of the upper layer 102 which define the sample window 110 and the viewing window 112 are more impervious to fluids. The compacted areas of the upper layer 102 along with the non-absorbent layer 106 about the periphery of the absorbent strip 104 thus form a channel tending to maintain fluids within the absorbent strip 104.

Figure 5:
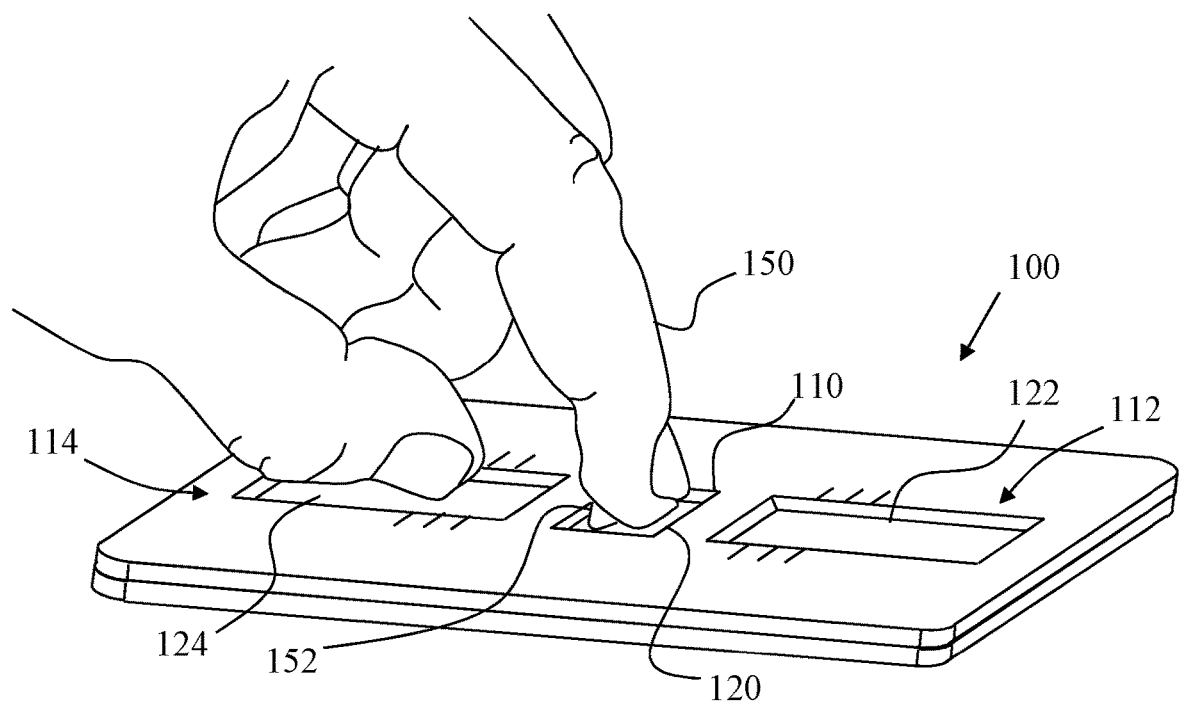
FIG. 5 depicts a perspective view of a user providing a blood sample onto the sample application portion of the absorbent strip of the collection card of FIG. 1 through a sample receiving window.

The assembled collection card may be packaged for storage until a fluid sample is needed. A fluid sample may be obtained in a clinical or laboratory setting. Alternatively, the collection card 100 may be used by lay persons at virtually any location. A sample is obtained by producing the fluid, such as by pricking a finger to obtain blood. By way of example, a finger 150 has been lanced to obtain a blood sample 152 in FIG. 5. The sample application portion 120 is then identified using a sample application portion indicium such as the sample receiving window 110. Drops of blood from the finger 150 are then dripped from above the collection card 100 through the sample receiving window 110 directly onto the absorbent strip 104 at the sample application portion 120.

When the fluid sample contacts the sample application portion 120, the sample is wicked by the absorbent strip 104, and preferentially aided in movement and separation by the chemical or physical nature of the non-absorbent layer 106, in two directions. A first portion of the sample wicks along the absorbent strip portion 122 away from the sample application portion 120 along the channel formed by the compacted areas of the upper layer 102 along with the non-absorbent layer 106 toward a location viewable through the sample viewing window 112. A second portion of the sample wicks along the absorbent strip portion 124 away from the sample application portion 120 along the channel formed by the compacted areas of the upper layer 102 along with the non-absorbent layer 106 toward a location viewable through the sample viewing window 114. As additional blood is placed into the sample application portion 120, the wicked fluid will become visible through the viewing windows 112/114.

The collection card 100 is configured to indicate to a user when a sufficient sample volume has been applied to the sample application portion 120. Accordingly, while a user can be instructed to place a certain volume of fluid into the sample application portion 120 (e.g., a specified number of blood drops), the user can alternatively simply wait until the wicking sample aligns with an indicium associated with a volume of the collected sample which, when absorbed by the absorbent strip, separates (for embodiments configured to separate sample components) into a component of the collected sample along the absorbent strip portion 122 to an extent sufficient to perform a test on the component. Because the sample wicks substantially equally along the absorbent strip portion 124, the same indicium will indicate that the component will also be separated along the absorbent strip portion 124 to an extent sufficient to perform a test on the component.

In one embodiment, the width of the bridge 116 and/or the width of the bridge 118 is configured to be the indicium. Thus, when fluid is observed through one or both of the sample viewing windows 112/114, sufficient sample has been applied to the sample application portion 120 to perform two tests.

For embodiments which are not configured to separate sample components, the indicium indicates when sufficient volume of sample has been applied to the sample application portion 120 for the desired test. Since there is no separation needed, the indicium will typically indicate sufficient volume for a single test.

Figure 6:
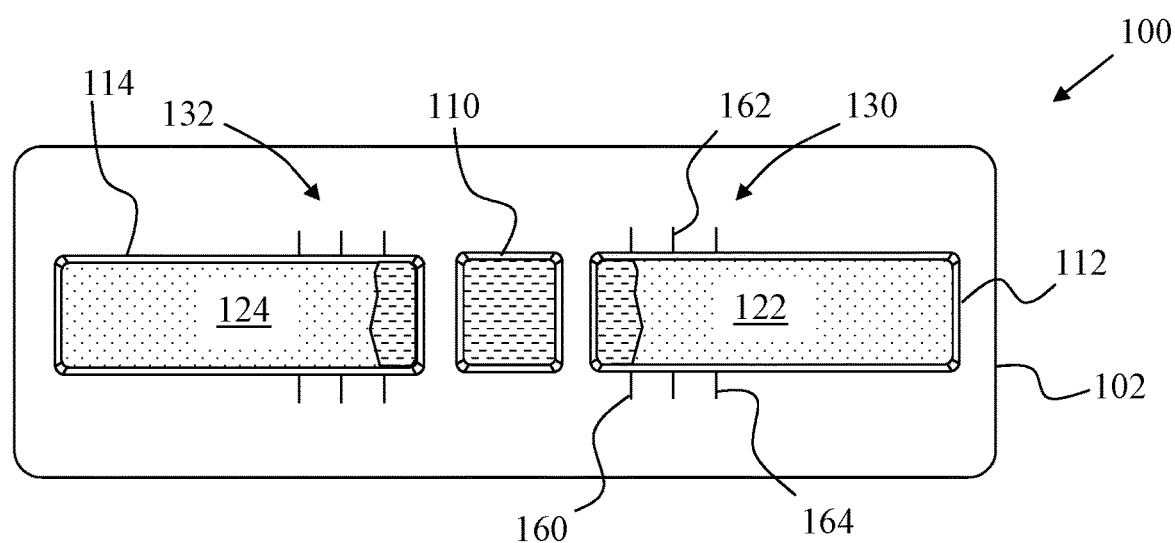
FIG. 6 depicts a top plan view of the collection card of FIG. 1 after sufficient fluid has been provided to the sample application portion of the absorbent strip through the sample receiving window to perform tests on components of the fluid that will be separated by the absorbent strip in accordance with principles of the disclosure.

In other embodiments, the reference marks 130/132 are provided as indicia either as an alternative to using the bridges 116/118 or in addition to using the bridges 116/118. Thus, in one embodiment once the fluid reaches the reference line 160 as shown in FIG. 6, sufficient blood has been absorbed to separate a quantity of plasma to perform two tests, one test using the absorbent strip portion 122 and a second test using the absorbent strip portion 124. The reference lines 162 and 164 may be provided to indicate when sufficient blood has been absorbed to separate a quantity of plasma necessary for performance of four tests and six tests, respectively.

As noted above, substantially equal amounts of the sample will flow along both of the flow paths toward the sample viewing windows 112/114. Accordingly, in some embodiments, the indicium is/are provided for only one of the sample viewing windows 112/114.

When the sample to be collected is blood, the amount of blood that is necessary to obtain a desired amount of plasma will vary based not only on the materials used, but also based upon the geometry of the channel formed. By way of example, by using materials identified above absorbent strips may be formed with a width of from about 0.6 centimeters to about 4 centimeters. Optimum separation of plasma, however, is obtained with a width of about 1 centimeter. By optimizing the separation of the plasma, less blood is needed to obtain a particular amount of plasma.

The length of the absorbent strip 104 is also a consideration in ensuring sufficient separation of a sample fluid. By way of example, as the volume of sample fluid deposited in the absorbent strip 104 increases, the red blood cells, in the case of blood, will travel further along the absorbent strip 104. Thus, to ensure that a sufficient separation of a sample fluid occurs in the event too much sample is provided, the length of the absorbent strip 104 may be increased.

Once the desired sample has been collected, the collection card 100 is left to dry in some embodiments. In applications where rapid drying is desired, the sample viewing windows 112/114 are preferably not covered. This allows the fluid sample to directly contact atmosphere in order to provide more rapid drying.

Figure 7:
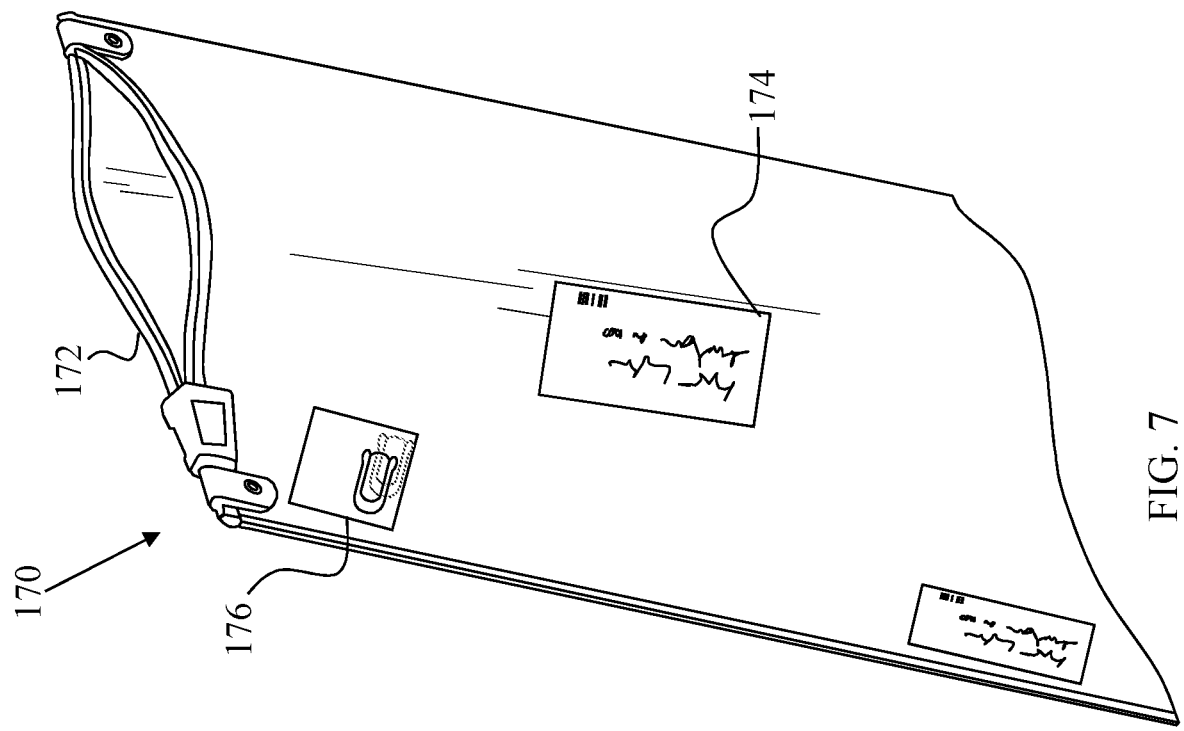
FIG. 7 depicts a perspective view of a resealable packet that may be used to transfer the collection card of FIG. 1 through a carrier service to a laboratory or other facility.

The collection card may then be shipped via any desired mode of transportation to a processing facility. A dried fluid sample contained in the absorbent strip 104 may be stored for a relatively long time without undue degradation of the sample. Nonetheless, the shelf life of the sample may be extended by placement of the collection card 100 in a storage container such as the package 170 shown in FIG. 7.

The package 170 is a gas impermeable package such as a plastic or foil package. The package 170 includes a resealable opening 172. The resealable opening 172 may include a tamper proof mechanism to provide an indication that the package 170 has been opened after a sample has been sealed therein. The package 170 is sized to accept the collection card 100 therein, and may be further dimensioned to allow for insertion into a flat envelope of standard size for automated processing by a postal facility. Alternatively, the package 170 may be configured to allow an address block 174 to be positioned on the package 170 along with postage 176. In some embodiments, one or more of the postage and address block are provided on the package.

In one embodiment, an oxygen scrubber (not shown) is provided with the package 170. An oxygen scrubber typically includes thin shavings including pieces of metal and a carrier desiccant that loosely holds some amount of water. When the package 170 is sealed with an oxygen scrubber therein, oxygen present within the package 170 reacts with the metal in the presence of water to form rust, thereby binding the oxygen. Elimination of oxygen from the atmosphere of the package 170 provides increased stability for various components within the dried fluid sample. For example, lipid analytes such as HDL, cholesterol, and triglycerides may be further stabilized by removal of oxygen from the atmosphere in which the sample is stored.

If desired, the collection card 100 may be placed within the package 170 and the package 170 sealed before a fluid sample within the absorbent strip 104 has been dried. Sealing the package 170 with a wet fluid sample held in the collection card 100 inhibits drying of the sample.

In accordance with one method a plurality of separated components of a fluid sample are obtained by receiving a collection card with an absorbent strip positioned on a nonabsorbent layer, typically at a processing facility. The collection card includes two separated components of the fluid sample and, in some embodiments, the separated components are dried.

An absorbent strip portion on a first side of an identified sample receiving portion of the absorbent strip including a separated component of the fluid sample is identified. The identified absorbent strip portion is typically spaced apart from the identified sample receiving portion. For example, when the sample is blood the red blood cells are typically located near the sample receiving portion while the plasma is located farther from the sample receiving portion. The identified absorbent strip portion is then detached from the absorbent strip.

Another absorbent strip portion on a second side of the identified sample receiving portion of the absorbent strip including a separated component of the fluid sample is also identified. This identified absorbent strip portion is also typically spaced apart from the identified sample receiving portion for the reasons set forth above. This identified absorbent strip portion is also detached from the absorbent strip.

Figure 8:
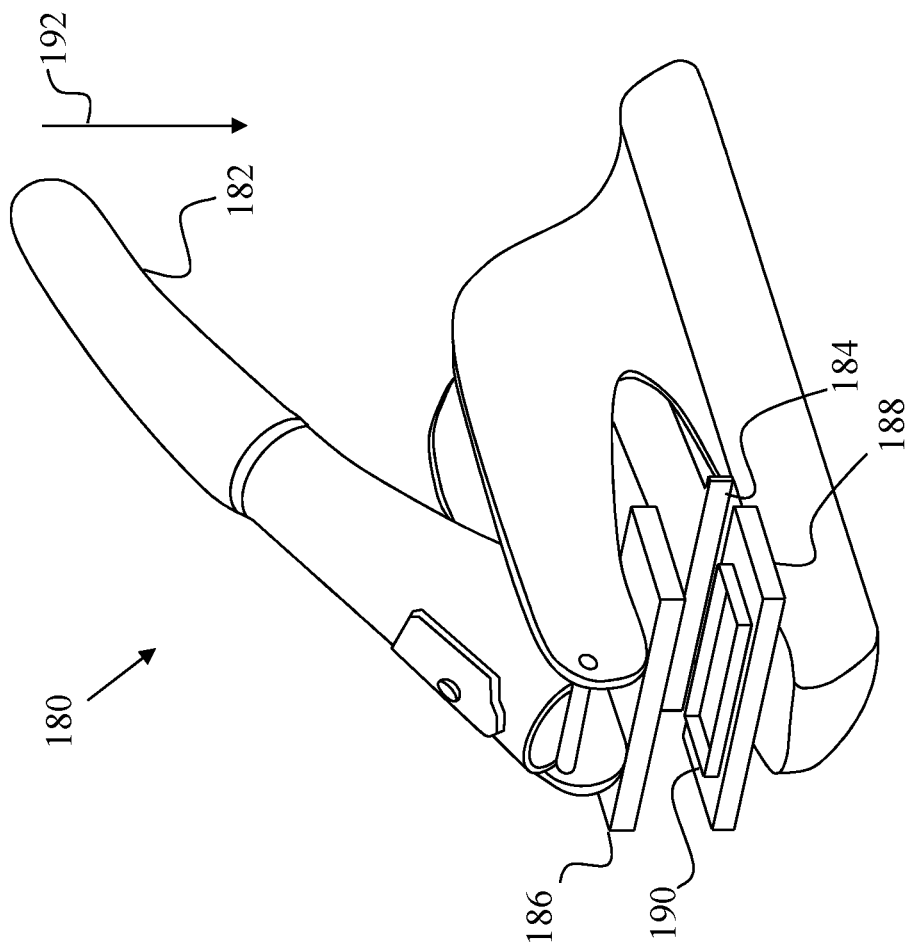
FIG. 8 depicts a perspective view of a removal tool that may be used to separate portions of the absorbent strip of the collection card of FIG. 1.

Removal of all or portions of the absorbent strip 104 from the collection card 100 for further processing is facilitated by the absence of an adherent between the absorbent strip 104 and any of the other components of the collection card 100. One device that may be used to remove the absorbent strip 104 is the removal tool 180 shown in FIG. 8. The removal tool 180 includes a lever arm 182, a guide stop 184, an upper mandrel 186 and a lower mandrel 188. The lower mandrel 188 includes a shaped cutting edge 190 which is sized to mate with the sample viewing window 112 and the sample viewing window 114. The upper mandrel 186 includes a protuberance (not shown) that is slightly smaller than the sample viewing windows 112/114 and positioned to fit within the shaped cutting edge 190.

Accordingly, removal of a portion of the absorbent strip 104 including a separated sample is accomplished by placement of the collection card 100 on the removal tool 180. Correct placement of the collection card 100 on the removal tool 180 may be guided by the guide stop 184. Alternatively, the sample viewing window 112/114 is simply positioned over the shaped cutting edge 190.

Thereafter, movement of the lever arm 182 in the direction of the arrow 192 forces the protuberance (not shown) on the upper mandrel 186 against the support layer 108 at a location aligned with the viewing window 112/114. The absorbent strip portion viewable through the viewing window 112/114 is thus forced against the shaped cutting edge 190 which separates a portion of the absorbent strip 104 including a separated sample from the collection card 100. The process is repeated for the other sample viewing window 112/114 to obtain a second absorbent strip portion. Portions of the support layer 108 and nonabsorbent layer 106 which are removed with the absorbent strip portions are then easily separated from the absorbent strip portions since there is no adhesive between the nonabsorbent layer 106 and the portions of the absorbent strip.

If desired, the entire absorbent strip 104 may be removed from the collection card 100 by separating at least one end of the bridges 116/118 and applying sufficient force against the support layer 108 to deform the upper layer 102 sufficiently to allow the absorbent strip 104 to move past the rims or lips 140 and 142. A punch type device similar to the removal tool 180 may be used for this purpose. The nonabsorbent layer will typically remain with the upper layer 102 and the support layer 108 since those components are adhered together. Thus, the absorbent strip is separated from the nonabsorbent layer 108 upon removal of the absorbent strip 104. The portions of the absorbent strip portions including the separated components are then separated from the absorbent strip in a manner similar to the process described above. In some embodiments, scissors, hole punches, or the like can be used to cutout the desired portions.

Various other modifications of the collection card 100 may be incorporated to optimize the collection card for particular tests. In one embodiment, polyhexamethylene biguanide hydrochloride (PHMB) is incorporated into the absorbent strip 104. PHMB is an additive used in bandages for inhibiting the growth of microbial organisms such as bacteria and fungi.

In a further embodiment, prior to blood or other biological fluid application, a polypeptide fraction of highly purified dermal collagen of porcine origin (Prionex from Pentapharm) is applied and dried to the collection card absorbent strip 104. A collection card 100 treated with Prionex applied to the absorbent strip 104 at a 0.1 percent concentration can yield close to double the separation area of serum or plasma for a given volume of blood applied to the absorbent strip 104. Other substances such as various proteins, detergents, salts or solvents, or other chemicals may also be used to enhance separation of a sample fluid.

Another additive that is useful when obtaining fluid samples in the form of blood is sucrose. In particular, cholesterol containing molecules and cholesterol itself are hydrophobic molecules which in pure form do not mix with an aqueous solution. The complex arrangement of proteins, salts and carbohydrate and complex carbohydrate in blood, however, holds these hydrophobic molecules in suspension. Disruption of these serum components during drying could result in clumping or aggregation of the hydrophobic molecules rendering successful hydration of the hydrophobic molecules problematic.

Application of sucrose in 1 to 10% wt./vol. concentration followed by drying to the absorbent strip 104, however, provides a more reproducible drying and rehydration of cholesterol containing molecules such as HDL, LDL and the cholesterol molecule itself. It is believed that the carbohydrate sucrose molecules are surrounded by water molecules when a fluid sample is added. Thus, the sucrose layers surround the hydrophobic cholesterol or triglyceride molecules during the drying and inhibit aggregation via hydrophobic binding of the sucrose shielded hydrophobic molecules.

While the present disclosure has been illustrated by the description of exemplary processes and system components, and while the various processes and components have been described in considerable detail, applicant does not intend to restrict or in any limit the scope of the appended claims to such detail. Additional advantages and modifications will also readily appear to those skilled in the art. The disclosure in its broadest aspects is therefore not limited to the specific details, implementations, or illustrative examples shown and described. For example, while only two flow paths are described, it is possible to provide additional flow paths. For example, an absorbent strip in the shape of a cross would provide four separated sample portions. Accordingly, departures may be made from such details without departing from the spirit or scope of applicant's general inventive concept.

The invention claimed is:

1. A method of collecting a fluid sample comprising:
identifying a sample application portion of an absorbent strip of a collection card using a sample application portion indicium;
applying a volume of fluid onto the sample application portion of the absorbent strip;
moving a first portion of the applied volume of fluid along a first absorbent strip portion coplanar with the sample application portion in a first plane and extending for a first length directly from the sample application portion and positioned on a nonabsorbent layer of the collection card, the nonabsorbent layer extending in a second plane parallel to the first plane and continuously contacting the first absorbent strip portion along the entire first length;
separating a first component of the first portion of the applied volume of fluid along the first absorbent strip portion while moving the first portion of the applied volume of fluid along the first absorbent strip portion;
moving a second portion of the applied volume of fluid along a second absorbent strip portion coplanar with the sample application portion in the first plane and extending for a second length directly from the sample application portion and positioned on the nonabsorbent layer, the nonabsorbent layer continuously contacting the first absorbent strip portion along the entire second length, wherein the second absorbent strip portion is spaced apart from the first absorbent strip portion by the sample application portion;
separating a second component of the second portion of the applied volume of fluid along the second absorbent strip portion while moving the second portion of the applied volume of fluid along the second absorbent strip portion;
drying the separated first component;
drying the separated second component; and
determining, prior to drying the separated first component, that a sufficient volume of fluid has been applied to the sample application portion to perform a test on the dried first component by viewing a portion of the first portion of the applied volume of fluid in the first absorbent strip portion.

2. The method of claim 1, wherein:
identifying the sample application portion comprises identifying a sample receiving portion in an upper layer of the collection card; and
applying the volume of fluid comprises applying the volume of fluid to the sample application portion from above the collection card through the sample receiving portion.

3. The method of claim 2, wherein:
drying the separated first component comprises exposing the separated first component directly to atmosphere through a first sample viewing window extending completely though the upper layer; and
drying the separated second component comprises exposing the separated second component directly to atmosphere through a second sample viewing window extending completely though the upper layer, the second sample viewing window spaced apart from the first sample viewing window.

4. The method of claim 2, wherein
determining that a sufficient volume of fluid has been applied to the sample application portion further comprises:
determining that a sufficient volume of fluid has been applied to the sample application portion to perform a test on the dried first component by viewing a portion of the first portion of the applied volume of fluid in the first absorbent strip portion through a first sample viewing window of the upper layer.

5. The method of claim 4, wherein determining that a sufficient volume of fluid has been applied to the sample application portion comprises:
using an indicium of the upper layer to determine that a sufficient volume of fluid has been applied to the sample application portion.

6. A method of obtaining a plurality of separated components of a fluid sample comprising:
receiving a collection card with an absorbent strip positioned on a nonabsorbent layer extending contiguously beneath a sample receiving portion of the absorbent strip, a first absorbent strip portion of the absorbent strip, and a second absorbent strip portion of the absorbent strip;
identifying the first absorbent strip portion on a first side of the sample receiving portion of the absorbent strip and spaced apart from the sample receiving portion, the first absorbent strip portion including a first separated component of a fluid sample;
detaching the identified first absorbent strip portion from the absorbent strip;

identifying the second absorbent strip portion on a second side of the sample receiving portion of the absorbent strip and spaced apart from the sample receiving portion, the second absorbent strip portion spaced apart from the first absorbent strip portion by the sample receiving portion, the second absorbent strip portion including a second separated component of the fluid sample; and detaching the identified second absorbent strip portion from the absorbent strip, wherein:

the first separated component of the fluid sample and the second separated component of the fluid sample are dried components of the fluid sample; and prior to drying the separated first component, a sufficient volume of fluid was determined to have been applied to the sample application portion to perform a test on the dried first component by viewing a portion of the first portion of the applied volume of fluid in the first absorbent strip portion.

7. The method of claim 6, wherein:

detaching the identified first absorbent strip portion comprises accessing the absorbent strip through a first window extending completely through an upper layer of the collection card, the identified first absorbent strip portion aligned with the first window; and detaching the identified second absorbent strip portion comprises accessing the absorbent strip through a second window extending completely through an upper layer of the collection card, the identified second absorbent strip portion aligned with the second window.

8. The method of claim 7, further comprising:

separating a first portion of the nonabsorbent layer from the detached first absorbent strip portion; and separating a second portion of the nonabsorbent layer from the detached second absorbent strip portion.

* * * * *